(12) United States Patent
Welches et al.

(10) Patent No.: US 8,190,243 B2
(45) Date of Patent: May 29, 2012

(54) THERMAL SURGICAL MONITORING

(75) Inventors: Richard Shaun Welches, Manchester, NH (US); James Henry Boll, Newton, MA (US)

(73) Assignee: Cynosure, Inc., Westford, MA (US)

( * ) Notice: Subject to any disclaimer, the term of this patent is extended or adjusted under 35 U.S.C. 154(b) by 814 days.

(21) Appl. No.: 12/135,967

(22) Filed: Jun. 9, 2008

(65) Prior Publication Data

US 2009/0024023 A1  Jan. 22, 2009

Related U.S. Application Data

(60) Provisional application No. 60/933,736, filed on Jun. 8, 2007, provisional application No. 60/987,596, filed on Nov. 13, 2007, provisional application No. 60/987,617, filed on Nov. 13, 2007, provisional application No. 60/987,819, filed on Nov. 14, 2007, provisional application No. 60/987,821, filed on Nov. 14, 2007, provisional application No. 61/018,729, filed on Jan. 3, 2008, provisional application No. 61/018,727, filed on Jan. 3, 2008.

(51) Int. Cl.
*A61B 6/00* (2006.01)
*A61B 18/18* (2006.01)

(52) U.S. Cl. ............. 600/474; 600/476; 606/10; 606/11

(58) Field of Classification Search ................. 600/160, 600/437, 474; 606/8–10; 382/154; 604/20
See application file for complete search history.

(56) References Cited

U.S. PATENT DOCUMENTS

| | | | |
|---|---|---|---|
| 4,122,853 A | 10/1978 | Smith | |
| 4,759,349 A | 7/1988 | Betz et al. | |
| 5,056,515 A | 10/1991 | Abel | |
| 5,191,883 A | 3/1993 | Lennox et al. | |
| 5,193,526 A | 3/1993 | Daikuzono | |
| 5,197,470 A | 3/1993 | Helfer et al. | |
| 5,209,748 A | 5/1993 | Daikuzono | |
| 5,222,953 A | 6/1993 | Dowlatshahi | |
| 5,257,991 A | 11/1993 | Fletcher et al. | |
| 5,284,154 A | 2/1994 | Raymond et al. | |
| 5,304,173 A | 4/1994 | Kittrell et al. | |
| 5,334,191 A | 8/1994 | Poppas et al. | |
| 5,368,031 A | 11/1994 | Cline et al. | |
| 5,409,481 A | 4/1995 | Poppas et al. | |

(Continued)

FOREIGN PATENT DOCUMENTS

EP   1057455   12/2000

(Continued)

OTHER PUBLICATIONS

Benjavitvilai,C., Riviere,C.N., "Fuzzy Calibration of Magnetometer in Presence of Surgical Microscope", 2005 27th Annual International Conference of the IEEE Engineering in Medicine and Biology Society (IEEE Cat. No. 05CH37611C), Shanghai, China, Aug. 31-Sep. 3, 2005.

(Continued)

*Primary Examiner* — Michael Rozanski
(74) *Attorney, Agent, or Firm* — John M. Garvey; K&L Gates LLP

(57) ABSTRACT

An apparatus is disclosed for monitoring a thermal surgical procedure including a thermal camera for monitoring temperature at a plurality of locations within at least a portion of a surgical field undergoing thermal surgical treatment and generating a series of thermal images based on said monitoring, a processor for processing the thermal images, and a display for displaying, in real time, a series of display images indicative of temperature at the plurality of positions.

25 Claims, 10 Drawing Sheets

U.S. PATENT DOCUMENTS

| | | |
|---|---|---|
| 5,421,337 A | 6/1995 | Richards-Kortum et al. |
| 5,421,339 A | 6/1995 | Ramanujam et al. |
| 5,423,805 A | 6/1995 | Brucker et al. |
| 5,456,682 A | 10/1995 | Edwards et al. |
| 5,489,256 A | 2/1996 | Adair |
| 5,499,313 A | 3/1996 | Kleinerman |
| 5,501,680 A | 3/1996 | Kurtz et al. |
| 5,540,681 A | 7/1996 | Strul et al. |
| 5,608,210 A | 3/1997 | Esparza et al. |
| 5,628,744 A | 5/1997 | Coleman et al. |
| 5,628,771 A | 5/1997 | Mizukawa et al. |
| 5,651,783 A | 7/1997 | Reynard |
| 5,662,643 A | 9/1997 | Kung et al. |
| 5,688,266 A | 11/1997 | Edwards et al. |
| 5,688,267 A | 11/1997 | Panescu et al. |
| 5,707,369 A | 1/1998 | Vaitekunas et al. |
| 5,776,129 A | 7/1998 | Mersch |
| 5,810,802 A | 9/1998 | Panescu et al. |
| 5,830,209 A | 11/1998 | Savage et al. |
| 5,837,001 A | 11/1998 | Mackey |
| 5,893,885 A | 4/1999 | Webster, Jr. |
| 5,928,222 A | 7/1999 | Kleinerman |
| 5,935,124 A | 8/1999 | Klumb et al. |
| 5,951,543 A | 9/1999 | Brauer |
| 5,971,976 A | 10/1999 | Wang et al. |
| 6,015,404 A | 1/2000 | Altshuler |
| 6,022,346 A | 2/2000 | Panescu et al. |
| 6,027,493 A | 2/2000 | Donitzky et al. |
| 6,112,123 A | 8/2000 | Kelleher et al. |
| 6,162,215 A | 12/2000 | Feng |
| 6,162,218 A | 12/2000 | Elbrecht et al. |
| 6,171,302 B1 | 1/2001 | Talpalriu et al. |
| 6,214,034 B1 | 4/2001 | Azar |
| 6,282,442 B1 | 8/2001 | Destefano et al. |
| 6,322,584 B2 | 11/2001 | Ingle et al. |
| 6,327,506 B1 | 12/2001 | Yogo et al. |
| 6,332,891 B1 | 12/2001 | Himes |
| 6,350,261 B1 | 2/2002 | Domankevitz et al. |
| 6,447,503 B1 | 9/2002 | Wynne et al. |
| 6,447,504 B1 | 9/2002 | Ben-Haim et al. |
| 6,475,211 B2 | 11/2002 | Chess et al. |
| 6,493,608 B1 | 12/2002 | Niemeyer |
| 6,503,269 B2 | 1/2003 | Nield et al. |
| 6,544,257 B2 | 4/2003 | Nagase et al. |
| 6,607,525 B2 | 8/2003 | Franco et al. |
| 6,669,685 B1 | 12/2003 | Rizoiu et al. |
| 6,682,524 B1 | 1/2004 | Elbrecht et al. |
| 6,685,722 B1 | 2/2004 | Rosenbluth et al. |
| 6,772,053 B2 | 8/2004 | Niemeyer |
| 6,872,203 B2 | 3/2005 | Shafirstein et al. |
| 6,905,492 B2 | 6/2005 | Zvuloni et al. |
| 6,974,450 B2 | 12/2005 | Weber et al. |
| 7,104,985 B2 | 9/2006 | Martinelli |
| 7,216,055 B1 | 5/2007 | Horton et al. |
| 7,217,265 B2 | 5/2007 | Hennings et al. |
| 7,280,866 B1 | 10/2007 | McIntosh et al. |
| 7,282,060 B2 | 10/2007 | DeBenedictis et al. |
| 7,282,723 B2 | 10/2007 | Schomacker et al. |
| 8,027,710 B1 | 9/2011 | Dannan |
| 2001/0007068 A1 | 7/2001 | Ota et al. |
| 2002/0019625 A1 | 2/2002 | Azar |
| 2002/0032437 A1 | 3/2002 | Andrews et al. |
| 2002/0173723 A1 | 11/2002 | Lewis |
| 2002/0173781 A1 | 11/2002 | Cense et al. |
| 2002/0173782 A1 | 11/2002 | Cense et al. |
| 2003/0028186 A1 | 2/2003 | Kreintel |
| 2003/0032950 A1 | 2/2003 | Altshuler et al. |
| 2003/0065314 A1 | 4/2003 | Altshuler et al. |
| 2003/0073989 A1 | 4/2003 | Hoey et al. |
| 2003/0187319 A1 | 10/2003 | Kaneko |
| 2003/0187383 A1 | 10/2003 | Weber et al. |
| 2004/0054248 A1 | 3/2004 | Kimchy et al. |
| 2004/0098070 A1 | 5/2004 | Mohr et al. |
| 2004/0111086 A1 | 6/2004 | Trombly |
| 2004/0122311 A1 | 6/2004 | Cosman |
| 2004/0143181 A1 | 7/2004 | Damasio et al. |
| 2004/0162490 A1 | 8/2004 | Soltz et al. |
| 2004/0167502 A1 | 8/2004 | Weckwerth et al. |
| 2004/0186465 A1 | 9/2004 | Francischelli et al. |
| 2004/0199079 A1 | 10/2004 | Chuck et al. |
| 2004/0199151 A1 | 10/2004 | Neuberger |
| 2004/0249261 A1 | 12/2004 | Torchia et al. |
| 2005/0065502 A1 | 3/2005 | Stoltz |
| 2005/0113815 A1 | 5/2005 | Ritchie et al. |
| 2005/0113890 A1 | 5/2005 | Ritchie et al. |
| 2005/0116673 A1 | 6/2005 | Carl et al. |
| 2005/0131400 A1 | 6/2005 | Hennings et al. |
| 2005/0143723 A1 | 6/2005 | Zvuloni et al. |
| 2005/0165315 A1 | 7/2005 | Zuluaga et al. |
| 2005/0171517 A1 | 8/2005 | Altshuler et al. |
| 2005/0203496 A1 | 9/2005 | Ritchie et al. |
| 2005/0203497 A1 | 9/2005 | Speeg et al. |
| 2005/0222556 A1 | 10/2005 | Arivra et al. |
| 2005/0245917 A1 | 11/2005 | Strassl et al. |
| 2005/0251116 A1 | 11/2005 | Steinke et al. |
| 2005/0257612 A1 | 11/2005 | Hiemer et al. |
| 2006/0052661 A1 | 3/2006 | Gannot et al. |
| 2006/0062448 A1 | 3/2006 | Hirsch et al. |
| 2006/0116671 A1 | 6/2006 | Slayton et al. |
| 2006/0118127 A1 | 6/2006 | Chinn |
| 2006/0173480 A1 | 8/2006 | Zhang |
| 2006/0224148 A1 | 10/2006 | Cho et al. |
| 2007/0093797 A1 | 4/2007 | Chan et al. |
| 2007/0123851 A1 | 5/2007 | Alejandro et al. |
| 2007/0179378 A1 | 8/2007 | Boese et al. |
| 2007/0208252 A1 | 9/2007 | Makower |
| 2007/0219602 A1 | 9/2007 | Ostrovsky et al. |
| 2007/0244527 A1 | 10/2007 | Hatayama et al. |
| 2007/0260230 A1 | 11/2007 | Youngquist et al. |
| 2007/0264625 A1 | 11/2007 | DeBenedictis et al. |
| 2008/0004608 A1 | 1/2008 | Dacquay et al. |
| 2008/0058782 A1 | 3/2008 | Frangineas et al. |

FOREIGN PATENT DOCUMENTS

EP 1650615 4/2006

OTHER PUBLICATIONS

Wei Tech Ang, Khosla,P.K., Riviere,C.N., "Kalman Filtering for Real-Time Orientation Tracking of Handheld Microsurgical Instrument", 2004 IEEE/RSJ International Conference on Intelligent Robots and Systems (IROS), Sendai, Japan, Sep. 28-Oct. 2, 2004.

Wei Tech Ang, Khosla,P.K., Riviere,C.N., "Design of All-Accelerometer Inertial Measurement Unit for Tremor Sensing in Hand-Held Microsurgical Instrument", 2003 IEEE International Conference on Robotics and Automation (vol,2), Taipei, Taiwan, Sep. 14-19, 2003.

International Search Report, PCT/US08/07218, Oct. 10, 2008.
International Search Report, PCT/US08/07219, Oct. 10, 2008.
International Search Report, PCT/US08/07225, Oct. 10, 2008.
International Search Report, PCT/US08/07226, Oct. 10, 2008.
International Search Report, PCT/US08/07227, Oct. 14, 2008.

THERMAL SURGICAL MONITORING

CROSS REFERENCE TO RELATED APPLICATIONS

The present application claims benefit to each of U.S. Provisional Application Ser. No. 60/987,596, filed Nov. 13, 2007, U.S. Provisional Application Ser. No. 60/987,617, filed Nov. 13, 2007, U.S. Provisional Application Ser. No. 60/987,819, filed Nov. 14, 2007, U.S. Provisional Application Ser. No. 60/987,821, filed Nov. 14, 2007, U.S. Provisional Application Ser. No. 61/018,727, filed Jan. 3, 2008, U.S. Provisional Application Ser. No. 61/018,729, filed Jan. 3, 2008, and U.S. Provisional Application Ser. No. 60/933,736, filed Jun. 8, 2007, the contents each of which are incorporated by reference herein in their entirety.

BACKGROUND

The present invention relates to a surgical theatre infrared (IR) camera and a surgical IR sensor. More particularly, the present invention relates to a surgical IR camera and sensor adapted to monitor a surface temperature of a patient for during a thermal surgical procedure.

Plastic surgeons, dermatologists and their patients continually search for new and improved methods for treating the effects of an aging or otherwise damaged skin. One common procedure for rejuvenating the appearance of aged or photo-damaged skin is laser skin resurfacing using a carbon dioxide laser. Another technique is non-ablative laser skin tightening, which does not take the top layer of skin off, but instead uses a deep-penetrating laser to treat the layers of skin beneath the outer epidermal layer, tightening the skin and reducing wrinkles to provide a more youthful appearance.

For such techniques for laser skin tightening treatment, it has been difficult to control the depth and amount of energy delivered to the collagen without also damaging or killing the dermal cells. Much of the energy of the treatment pulse is wasted due to scattering and absorption in the outer epidermal layer, and the relatively high pulse energy required to penetrate this outer layer can cause pain and epidermal damage.

Some skin tightening techniques include using a hollow tubular cannula that contains an optical fiber connected to a laser source. The cannula can be inserted subcutaneously into a patient so that the end of the fiber is located within the tissue underlying the dermis. The source emits a treatment output, for example an output pulse that is conveyed by the fiber to the dermis, which causes collagen shrinkage within the treatment area, thus tightening the skin.

To improve one's health or shape, patients have also turned to surgical methods for removing undesirable tissue from areas of their body. For example, to remove fat tissue, some patients have preferred liposuction, a procedure in which fat is removed by suction mechanism because despite strenuous dieting and exercise, some of the patients cannot lose fat, particularly in certain areas. Alternatively, laser or other light sources has been applied for heating, removal, destruction (for example, killing), photocoagulation, eradication or otherwise treating (hereinafter collectively referred as "treating" or "treatment") the tissue.

In applications including those mentioned above, it is often desirable to monitor the temperature of a specific location, for example, a location within a surgical field, in real time. Such monitoring may prevent, for example, skin or other tissue damaged caused by, for example, overheating.

SUMMARY

The inventors have realized that a thermo-surgical theater and IR sensor may provide hands free surface temperature monitoring and/or feedback to a surgeon during thermal surgical procedures, for example laser surgery or any other procedure/surgery where energy is deposited into surface tissue to effect a tissue temperature rise. Various embodiments could include surgical systems employing, e.g., laser, radio frequency (RF), acoustic or other suitable energy source.

In some embodiments, an apparatus for monitoring a thermal surgical procedure includes a thermal camera for monitoring temperature at a plurality of locations within at least a portion of a surgical field undergoing thermal surgical treatment and generating a series of thermal images based on the monitoring. The apparatus further includes a processor for processing the thermal images and a display for displaying, in real time, a series of display images indicative of temperature at the plurality of positions.

In some embodiments, the display images indicative of temperature at the plurality of locations comprise false color images. In some embodiments, the thermal camera is an infrared camera. In some embodiments, the thermal camera generates the series of thermal images at a rate of greater than about 30 frames per second. In some embodiments, the display displays the series of display images at a rate of greater than about 30 frames per second.

In some embodiments, the apparatus for monitoring a thermal surgical procedure further includes a video camera for monitoring at least a portion of the surgical field, where the display is configured to display, in real time, video images of said portion of the surgical field.

In some embodiments, the apparatus for monitoring a thermal surgical procedure further includes a processor configured to superimpose the thermal images with the video images, where the display images comprise the superimposed images.

In some embodiments, the field of view of the thermal camera substantially overlaps the field of view of the video camera.

In some embodiments, the apparatus for monitoring a thermal surgical procedure further includes an optical element which selectively directs light from the surgical field in the infrared spectrum to the thermal camera, and selectively directs light from the surgical field in the visible spectrum to the video camera. In some embodiments, at least one of the thermal camera and the video camera include an autofocus. In some embodiments, the apparatus for monitoring a thermal surgical procedure further includes a servo unit for directing the thermal camera to monitor a selected portion of the surgical field.

In some embodiments, the apparatus for monitoring a thermal surgical procedure further includes an indicator which illuminates the selected portion of the surgical field, where the servo unit comprises a tracking unit adapted to track the illuminated portion and direct the thermal camera to monitor the selected portion.

In some embodiments, the processor determines temperature information about the portion of the surgical field based on the thermal images. In some embodiments, the processor is coupled to a laser surgical device and is configured to control the operation of the laser surgical device based on said temperature information. In some embodiments, the processor is configured to process the thermal images and determine information indicative of temperature at the plurality of locations, compare the information indicative of temperature at the plurality of locations to a selected master threshold temperature, and produce a master alarm if the temperature at any of the plurality of locations exceeds the selected master threshold temperature.

In some embodiments, the processor is coupled to a laser surgical device and is configured to control the operation of the laser surgical device in response to the master alarm. In some embodiments, the processor is configured to process the thermal images and determine information indicative of temperature at a subset of the plurality of locations, compare the information indicative of temperature at the subset of plurality of locations to a selected range of temperature, and produce a range alarm if the temperature at any of the subset of the plurality of locations falls outside the selected range.

In some embodiments, the processor is coupled to a laser surgical device and is configured to control the operation of the laser surgical device in response to the range alarm. In some embodiments, the processor is configured to process the thermal images and determine information indicative of a rate of change of temperature at the plurality of locations, compare the information indicative of temperature at the plurality of locations to a selected secondary threshold temperature, compare the information indicative of the rate of change of temperature at the plurality of locations to a selected threshold rate, and produce a rate alarm if, at any one of the plurality of locations, the temperature exceeds the secondary threshold and the rate of change of temperature exceed the rate threshold. In some embodiments, the processor is coupled to a laser surgical device and is configured to control the operation of the laser surgical device in response to the rate alarm.

In some embodiments, the display comprises at least one chosen from the group consisting of: a video monitor, a flat panel monitor, a heads up display, and a virtual reality display.

In some embodiments, a method is defined for monitoring a thermal surgical procedure including using a thermal camera to monitor temperature at a plurality of locations within at least a portion of a surgical field undergoing thermal surgical treatment and generating a series of thermal images based on the monitoring, and displaying, in real time, a series of display images indicative of temperature at the plurality of positions based on the series of thermal images. In some embodiments, displaying, in real time, a series of display images indicative of temperature at the plurality of positions includes displaying false color images.

In some embodiments, the method further includes using a video camera to monitor at least a portion of the surgical field and displaying, in real time, video images of the portion of the surgical field. In some embodiments, the method further includes processing the thermal images and the video images to superimpose the thermal images with the video images and displaying display images corresponding to the superimposed images.

In some embodiments, the method further includes determining temperature information about the portion of the surgical field based on the thermal images. In some embodiments, the method further includes controlling the operation of a laser surgical device based on the temperature information.

In some embodiments, the method further includes processing the thermal images and determining information indicative of temperature at the plurality of locations, comparing the information indicative of temperature at the plurality of locations to a selected master threshold temperature, and producing a master alarm if the temperature at any of the plurality of locations exceeds the selected master threshold temperature.

In some embodiments, the method further includes processing the thermal images and determining information indicative of temperature at a subset of the plurality of locations, comparing the information indicative of temperature at the subset of plurality of locations to a selected range of temperature, and producing a range alarm if the temperature at any of the subset of the plurality of locations falls outside the selected range.

In some embodiments, the method further includes processing the thermal images and determine information indicative of a rate of change of temperature at the plurality of locations, comparing the information indicative of temperature at the plurality of locations to a selected secondary threshold temperature, comparing the information indicative of the rate of change of temperature at the plurality of locations to a selected rate threshold, and producing a rate alarm if, at any one of the plurality of locations, the temperature exceeds the secondary threshold and the rate of change of temperature exceed the rate threshold.

In some embodiments, the method further includes providing an indicator identifying a area of interest within the surgical field, tracking the position of the indicator, and adjusting the thermal camera to monitor the area of interest.

In some embodiments, an apparatus for monitoring temperature at a surface includes a temperature sensor for remotely sensing the temperature of an area of the surface, a light source for illuminating a of portion of the surface proximal to said area, and an indicator for providing information indicative of the temperature of the area sensed by the temperature sensor.

In some embodiments, the apparatus for monitoring temperature at a surface further includes a headpiece adapted to be worn by a user, where the temperature sensor, light source, and indicator are integrated with the headpiece. In some embodiments, the headpiece is a pair of eyewear, where the light source is positioned to illuminate a portion of the surface within a field of view of a wearer of the eyewear. In some embodiments, the eyewear includes a nose bridge, and the light source and temperature sensor are mounted on the nose bridge.

In some embodiments, the indicator includes a modulator which modulates the light source, where the modulation has one or more modulation properties which depend on the temperature sensed by the temperature sensor. In some embodiments, at least one of the modulation properties is selected from the group consisting of: modulation rate and modulation duty cycle.

In some embodiments, the indicator comprises a tone generator configured to produce an audible tone having one or more characteristics which depends on the temperature sensed by the temperature sensor. One or more characteristics may include at least one chosen from the group consisting of: frequency, modulation rate, modulation duty cycle, volume. In some embodiments, the indicator comprises a visual display which depends on the temperature sensed by the temperature sensor. In some embodiments, the visual display comprises a digital display positioned on the headpiece.

In some embodiments, the apparatus for monitoring temperature at a surface further includes a sensor for sensing information indicative of the spatial orientation of the headpiece, and a controller configured to control the output of the light source based on the information indicative of the spatial orientation of the headpiece.

In some embodiments, the apparatus for monitoring temperature at a surface further includes a monitor unit adapted to compare the temperature sensed by the sensor to a selected threshold temperature and produce an alarm based on the comparison. In some embodiments, the apparatus for monitoring temperature at a surface further includes a controller in communication with the monitor unit for adjusting the selected threshold temperature. In some embodiments, the controller is integral with the headpiece.

In some embodiments, the alarm is selected from the group consisting of: an audible alarm indication and a visual alarm indication. In some embodiments, the monitor unit is in communication with a thermal surgical device to control said device based on the sensed temperature. In some embodiments, the monitor unit is configured to inhibit operation of the thermal surgical device if the sensed temperature is greater than a selected threshold temperature.

In some embodiments, a method for monitoring tissue temperature during a thermal surgical procedure to be performed by an operator is defined, which includes providing headwear for the operator, the headwear itself including: a temperature sensor for remotely sensing the temperature of an area of a surface within a surgical field, a light source for illuminating a of portion of the surface proximal to the area of a surface within a surgical field, and an indicator for providing information indicative of the temperature of the area sensed by the temperature sensor. The method further includes directing the light source to illuminate an area of interest within the surgical field, using the temperature sensor to remotely sense the temperature of the area of interest, and using the indicator to provide information indicative of the temperature of the area.

In some embodiments, the method further includes modulating the light source, where the modulation has one or more modulation properties which depend on the sensed temperature of the area of interest. In some embodiments, the method further includes comparing the sensed temperature of the area of interest to a selected threshold temperature and providing an alarm based on the comparison. In some embodiments, the method further includes controlling the operation of a thermal surgical device based on the sensed temperature of the area of interest.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

Figure 1:
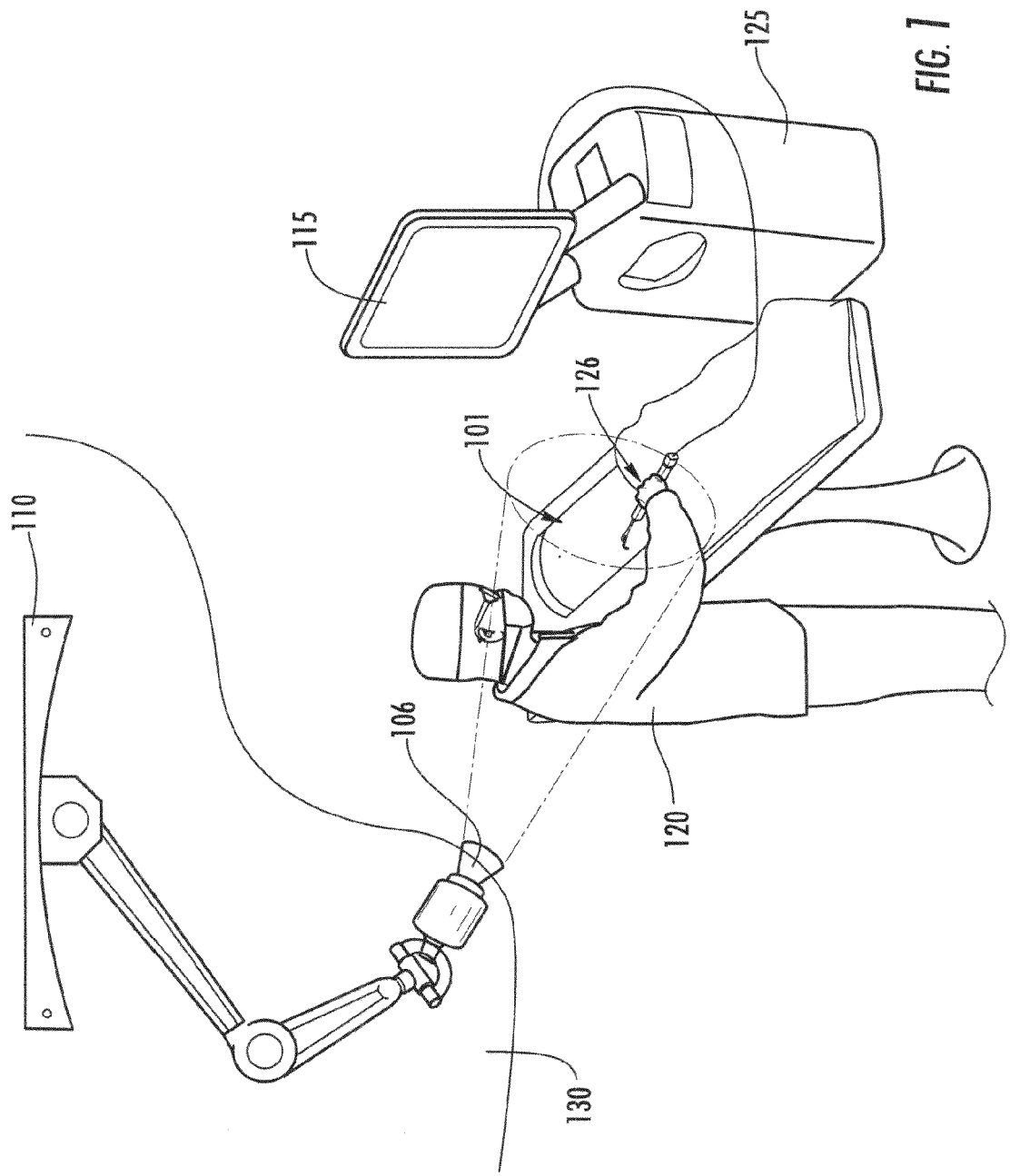
FIG. 1 shows a thermal surgical monitoring system.

FIG. 1 shows a thermal surgical monitoring system 100. A surgeon performs a thermal surgical procedure within surgical field 101. In the embodiment shown, laser light generated by a laser 125 is directed to through handpiece 126 to tissue within surgical field 101. Handpiece 126 includes a cannula for insertion into the patient through an incision located in surgical field 126. The cannula contains a waveguide, e.g. an optical fiber, which delivers later light from laser 125 to tissue to be treated. Accordingly, laser 125 may be used, for example, to treat tissues within the dermis to cause skin tightening, for laser lipolysis, or for other such applications.

System 100 measures temperatures at positions within surgical field 101 with thermal camera 105 (e.g. a thermal camera) which is, in some embodiments, mounted to a ceiling 110 above a surgical site. An exemplary suitable thermal camera is a high resolution infrared (IR) camera such as the ThermaCam45 Infrared Camera, manufactured by FLIR, Wilsonville, Oreg., which produces both good resolution and a wide field of view.

Display 115 (e.g. an LCD screen) is located within convenient view of a surgeon 120 such that a real time surface temperature information in the form of, for example, a false color isotherm map shown on display 115 is available to the surgeon during surgery. The surgeon can use the real time surface temperature information to control a deposition of energy within surgical field 101 in a tissue or tissues to be treated, such that, for example, a desired temperature rise in the treated tissue or tissues is achieved.

In some embodiments, the thermal camera 105 includes an auto focus 106. In typical applications practical difficulties regarding, e.g., the sterility of surgical field 101 and accessibility of thermal cameral 105 make such a feature, allowing hands free operation, desirable. In some embodiments, thermal camera 105 includes a manual focus control, e.g. a zoom lever. Such a control could be covered with a sterile bag 130. In some embodiments, thermal camera 105 has a preset depth of field that would include the full surgical working range, reducing or eliminating the need for an auto focus feature 106.

In some embodiments, the mounting location for thermal camera 105 would be over a surgical arena adjacent to or part of a set of ceiling mounted surgical lights. As an example, the camera may be light enough to mount to existing operating room (OR) lighting booms. In some embodiments, a ceiling mounted camera boom places the thermal camera 105 advantageously close to a surgical field 101, yet out of the way of the surgeon. In various embodiments, the display 115 can also be ceiling boom mounted. In some embodiments, the display 115 may be mounted on top of treatment laser 125.

In various embodiments, a wide angle or standard lens may be used to provide a suitable view for typical surgical applications, roughly framing a human abdomen, for example, at a working distance of 3-6 feet. In some embodiments, a temperature measurement accuracy may be approximately ±2° C., with a temperature drift over a 1 hour period of ±2° C. Some embodiments may feature a calibration shutter which operates, for example, about every minute. Some embodiments may feature less frequent calibration, more suitable for the particular application at hand.

In typical thermal surgical applications, providing real time surface temperature information is important because the large number of uncontrollable variations in surgery such as inhomogeneities in skin type, circulation/dilation, skin thickness, fibrotic tissue, geometry of surgical instruments with respect to anatomical structures, and surgical technique all effect the resulting temperature rise for a given energy input. For this reason, system 100 provides real time surface temperature information which can be used as "feedback" by the surgeon performing the treatment procedure. By monitoring the surface temperature directly, the treatment can be improved or optimized for safety and efficacy. In some embodiments, the surgeon manually adjusts his actions based on the displayed temperature information (e.g. by adjusting applied dosage). As discussed in detail below, in some embodiments, temperature information measured by system 100 may be processed and used to provide alerts to the surgeon and/or automatically control laser 125 (e.g. to shut off the laser system in the event of the appearance of a high temperature "hot spot" in within surgical field 101).

Figure 2:
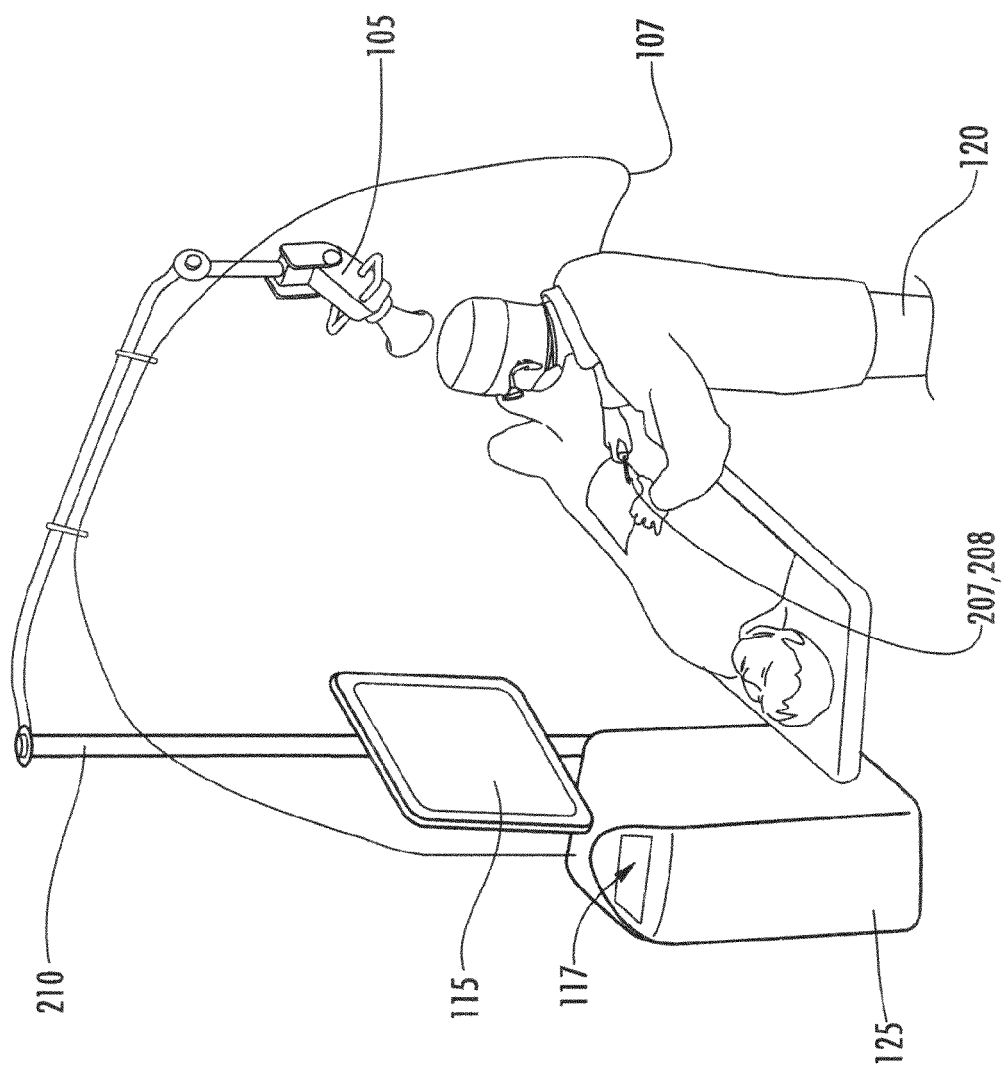
FIG. 2 shows a thermal surgical monitoring system with a surgical theatre thermal camera and laser treatment instrument mounted to an adjustable pole.

FIG. 2 shows and embodiment of system 100 where thermal camera 105 is mounted on an adjustable pole 210 connected to laser 125. Such mounting may reduce or eliminate operating room installation costs and issues concerning the surgical sterile field. In some embodiments, thermal camera 105 may be controlled (e.g., turned On/Off) directly from touchscreen display 117 on the laser 125. In such configurations, laser 125 and system 100 are integrated such that no external wiring above and beyond a self contained wiring for the laser 125 may be required.

Figure 2A:
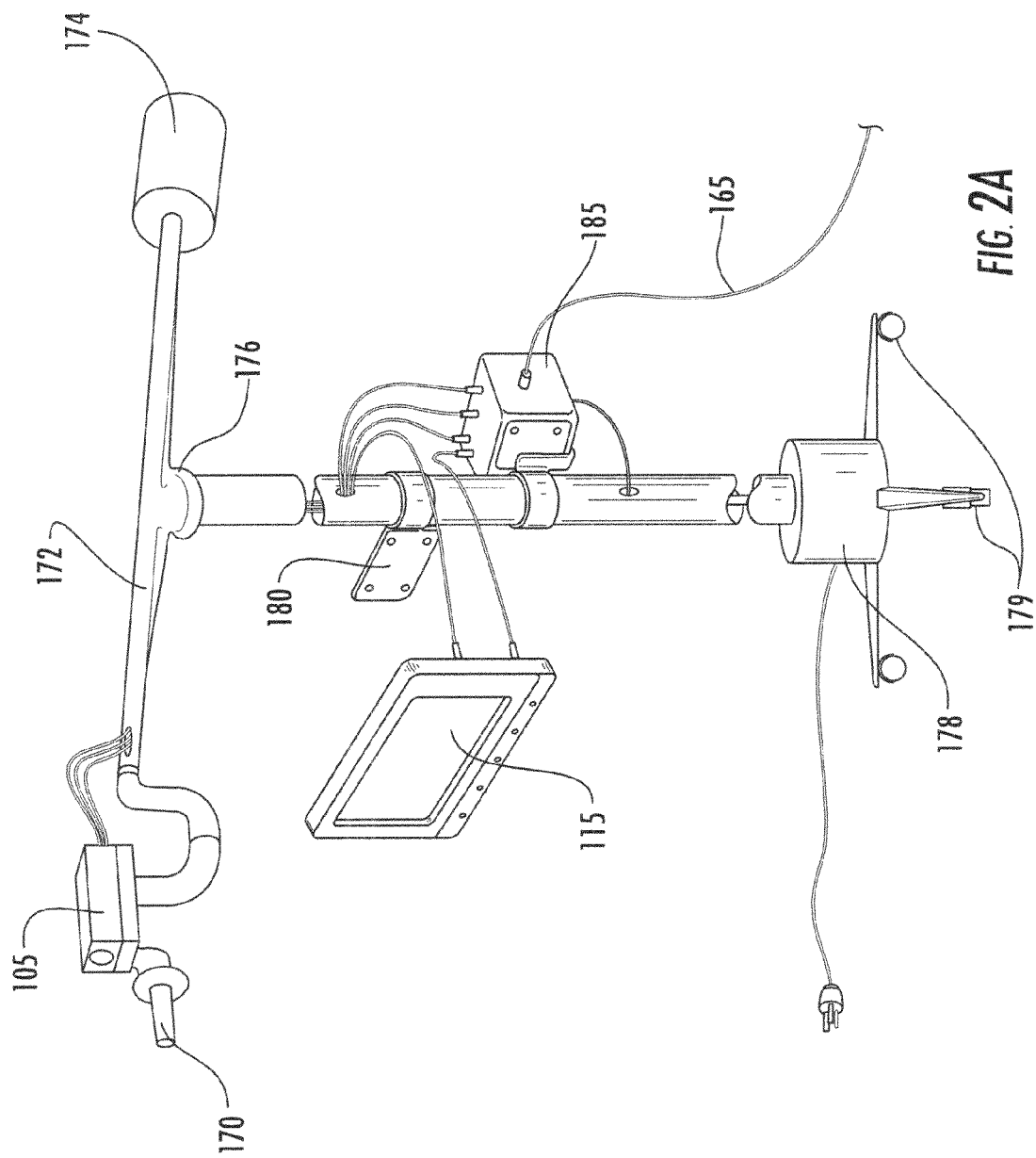
FIG. 2A shows a thermal surgical monitoring system with a surgical theatre thermal camera and laser treatment instrument mounted to a portable station.

FIG. 2A shows a thermal surgical monitoring system with a surgical theatre thermal camera and laser treatment instrument mounted to a portable station 165. An autoclavable handle 170 allows for the adjustment of the thermal camera 105. The thermal camera 105 itself is supported and balanced by a boom 172 and counterweight 174, respectively, that allows the thermal camera 105 to pivot about a portable station pivot point 176. The bottom of the portable station 165 is configured with a support ballast 178 and a set of castors 179 to both stabilize the portable station 165 and to give it portability.

A display 115 is connected to the portable station 165 to a mounting bracket 180 approximately eye level to the surgeon 120. A processor 180 to interface the thermal camera 105 to the display 115 and the laser 125 and to interface the display 115 to the laser 125 is mounted to a back side of the portable station 165.

Figure 3:
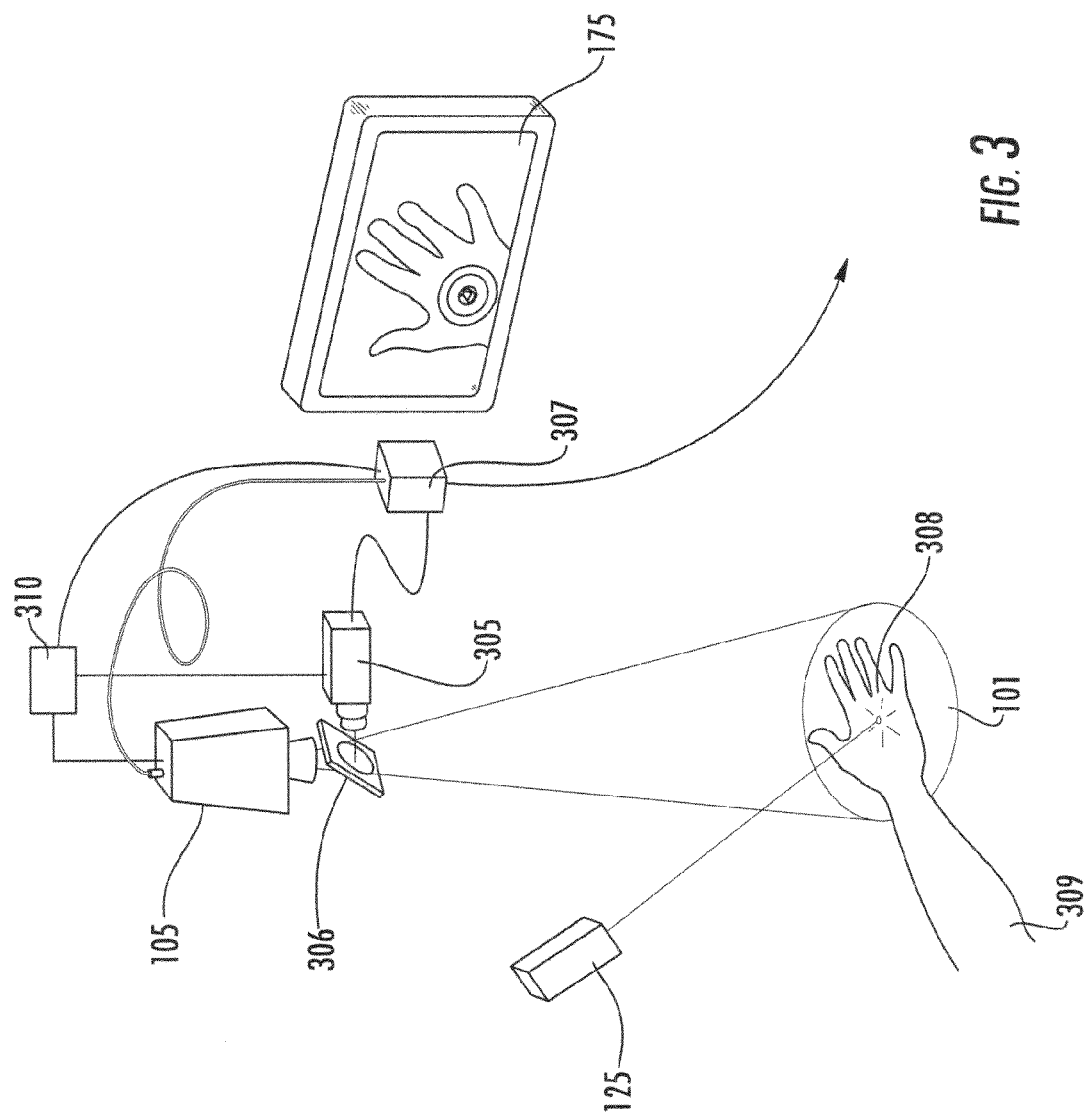
FIG. 3 shows a display of a thermal image taken with a surgical theatre thermal camera superimposed onto a display of a video image of a treatment site taken with a video camera.

FIG. 3 shows an embodiment of system 100 featuring a conventional video camera 305 (e.g. operating within the visual spectrum) in addition to thermal camera 105. This allows a simultaneous display (e.g. superposition) of a thermal image (e.g. a false color image) taken with thermal cameral 105 and a video image of a treatment site taken with a video camera. As shown, thermal camera 105 is ceiling mounted 110 at right angles to the standard video camera 305. Light from surgical field 101 is directed to thermal camera 105 and standard video camera 305 using beam splitting optic 306. For example, light in the IR spectrum may be selectively directed to thermal camera 105 while light in the visible spectrum is directed to conventional camera 305. The optic 306 may be made of ZnSe or Germanium, both of which have good IR transmission, and both of which can be coated to reflect the visible wavelengths. If the visible full-color spectrum is distorted due to a coating or to a substrate reflectivity, a black and white standard video image would, in some embodiments, suffice.

As shown, the two cameras 105, 305 have a set of matched field of views 308, preferably with a working range of several feet, reducing the need to refocus the cameras. The laser 125 irradiates a target tissue 309 in the field of view 308. The video images of the two cameras may be processed by a processor 307, which may combine the images for display on display 115. Processor 307 may include high speed image processing capabilities to combine and analyze a set of real time images for potential for hot spots. In some embodiments processor 307 may control laser 125 based on information determined by processing the images. In some embodiments, no connection is made from the laser driver 307 to the laser 125. In the case where no connection is made, the laser driver provides temperature and position data to the surgeon, displaying the temperature and position data on the display 115.

Although a particular arrangement of cameras 105 and 305 is shown, other arrangements are possible. For example, some embodiments may feature a stereoscopic version using, for example, a standard video camera (visual spectrum) 305 in sync and aligned immediately adjacent to the thermal camera 105. In some embodiments, both the standard video camera 305 and the thermal camera 105 have the same field of view.

In some embodiments, images from video camera 305 may be displayed on display 115 superimposed with images from thermal camera 105. For example, in some embodiments, an image from thermal camera 105 can be a transparent layer of false color superimposed on top of an image from the standard video camera 305. In this way, a set of hot spot islands could be immediately linked to a corresponding anatomical treatment area without a need to use other indicia (e.g. a warm or cold cannula placed within the field of view) to identify where the hot spots are located.

As discussed below, in some embodiments, images superimposed from thermal camera 105 onto images from the standard video camera 305 provide data to a laser driver 307 to determine laser power levels as a function of a set of treatment site surface temperatures. Controlling the laser 125 based on a set of treatment site surface temperatures may improve safety and efficacy.

In various embodiments, other display arrangements may be used. In some applications, an image from the standard video camera 305 and an image from the thermal camera 105 can be displayed side-by-side; in some applications, an image from the standard video camera 305 and an image from the thermal camera 105 can be displayed using a screen-in-screen format.

In another embodiment, display 115 is virtual reality image projection display. Such displays are commonly available and are low cost. In some embodiments, the thermal data for a virtual reality image projection is a three dimensional (3D) projection superimposed onto a 3D projection of the target tissue 309. In another embodiment, display 115 is a head mounted heads-up display (HUD) used to superimpose a set of images from the thermal camera directly onto the target tissue 309 in the field of view of the surgeon. A focal distance for the HUD may be set approximately to the distance from the eyes of the surgeon 120 to the target tissue 309.

In some embodiments, a servo driven stereo camera assembly 310, supporting both the thermal camera 105 and the standard video camera 305, allows for automatic tracking and auto focus of the target tissue 309. The stereo camera assembly may, for example, track an aim beam, directed from the laser 125, and position such that the thermal camera is focused on the target tissue with a 10-15 cm diameter field of view 308. In embodiments featuring an surgical device used internally (e.g. the cannula with fiber optic described above) an aim beam may be used with sufficient intensity to shine through tissue and to provide a visible indicia of illumination on the outside of the patients skin. By tracking the aim beam and automatically focusing on a corresponding treatment area, system 100 provides a higher resolution thermal data and greater ease of use in the surgical theater.

Figure 3A:
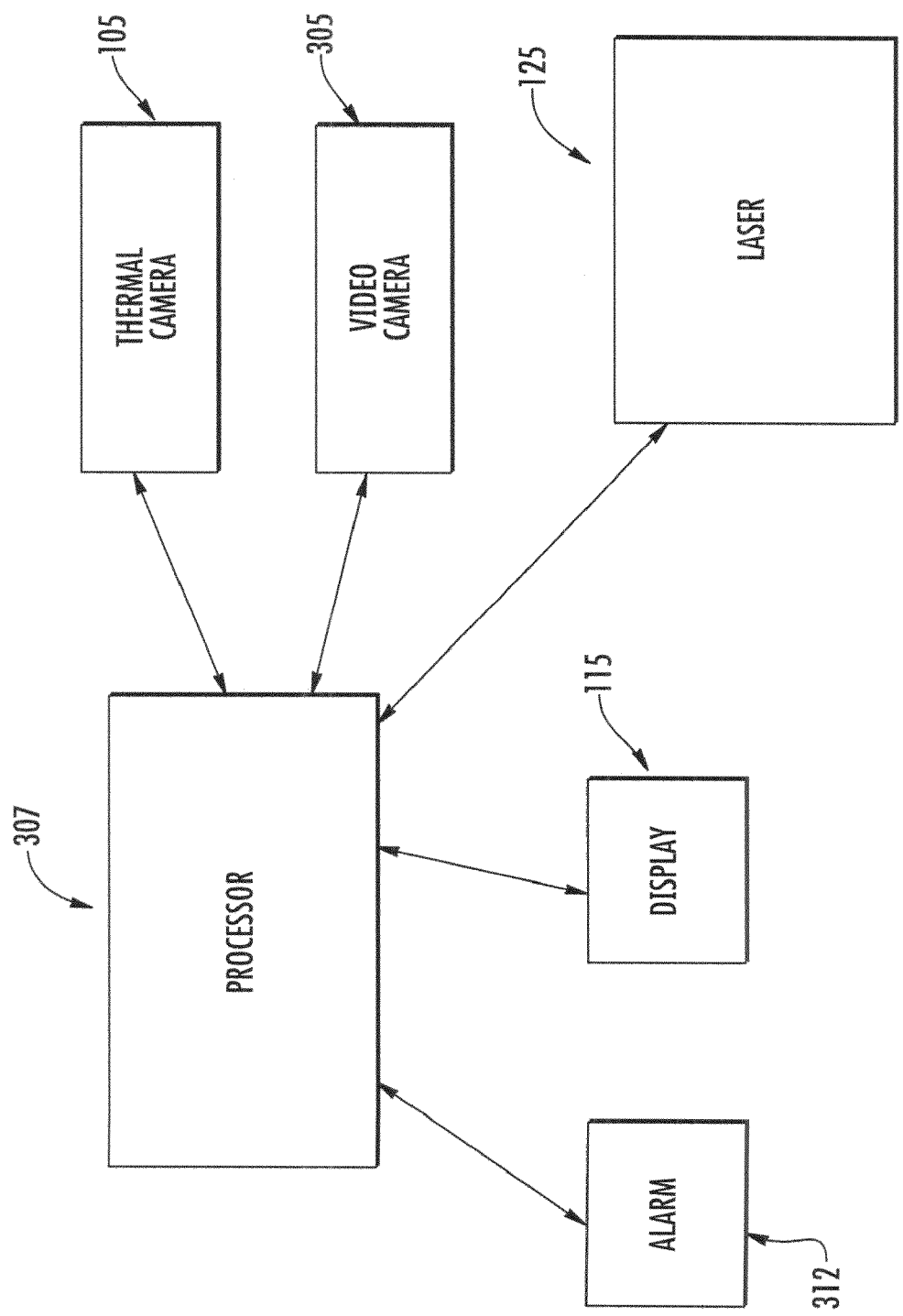
FIG. 3A shows a block diagram of a thermal surgical monitoring system with feedback control to a thermal surgical device.

As noted above, in various embodiments, processing of thermal data taken from thermal camera allows for numerous types of alarms, thresholds and/or automatic control of a surgical device (e.g. laser 125) based on temperature information derived from the thermal images. For example, referring to FIG. 3A, thermal images from thermal camera 105 and, optionally. video images from video camera 305 are sent to processor 307. Processor 307 processes the images to determine temperature information about the portion of the surgical field 101 within thermal camera's field of view. For example, the processor may determine, in real time, the temperature and/or change in temper at all positions (or a subset thereof) within the field of view.

The processor may analyze this temperature information and provide alarms or other indications to the surgeon. For example, still referring to FIG. 3A, processor 307 is in communication with display 115, and can display information or alarm indications on the display based on the analyzed temperature information. For example, visual indications could be provided on the display highlighting "hot spot" locations within the filed of view having temperatures above a selected threshold. Processor 307 may also be in communication with separate alarm unit 312. Alarm unit 312 may provide a visual alarm indication (e.g. a flashing light), an audible alarm indication (e.g. a buzzer or tone generator), or any other suitable indication.

Processor 307 may also control laser 125 based on the analyzed temperature information. For example, the processor may be programmed to shut down the laser if the presence of one or more hot spots are detected. The processor may, in general, control any aspect of the laser (e.g. wavelength, pulse rate, intensity, etc.) based on the analyzed temperature data. In some embodiments processor 307 may receive other inputs from, e.g. acceleration, speed, or position sensors located in handpiece 126, thermal sensors located in handpiece 126, tissue type sensors located in handpiece 126, etc. Processor 307 may analyze information from these sensor inputs in conjunction with the temperature information from the thermal camera and display information, provide alarms, and/or control laser 125 based on the analysis.

For example, in some embodiments, the laser 125 may be directed by the processor 307 to automatically self limit the laser power applied to the target tissue 309. The laser driver 307 automatically adjusts the laser 125 power to achieve a selected surface sector temperature within the field of view 308. The surgeon 120 may thereby select a treatment area by for example, aiming a treatment beam or simply placing a surgical waveguide into the selected treatment sector and stepping on a footswitch. In some such embodiments, the system may also be optionally placed in a manual mode are where the surgeon 120 is in direct control of the laser 125.

The following describes a number of exemplary alarm settings which are useful in various thermal surgical setting.

Some embodiments may feature a master alarm, where an alarm occurs when any point within the thermal camera field of view exceeds a threshold, for example 48° C. In some embodiments, the alarm is not user selectable (i.e. hard-wired). It is possible that the threshold is exceeded as a result of a hot cannula 207, which may be a result of a surgical waveguide 208 slipping in the cannula 207 as the surgical waveguide is plunged in and out of the tissue. In some embodiments, a false alarm resulting from a hot cannula 207 may be reduced or eliminated by weighting the points within the thermal camera field of view, allowing for localized hot spots that do not set off the alarm.

Some embodiments feature a "fast alarm", where an alarm occurs when any point within the thermal camera field of view exceeds a threshold, for example 45° C., and a rapid rate of change of temperature ($\Delta T$) is detected in within the thermal camera field of view. In some embodiments, the fast alarm is not user selectable. In some embodiments, $\Delta T$ is approximately 0.2° C./min.; $\Delta T$ on the order of 0.2° C./min. may detect a leakage of a set of warm fluids from an incision site. Further, a $\Delta T$ on the order of 0.2° C./min. may give an indirect indication of an excessive internal deep tissue temperature, as a deep tissue temperature may appear in a high resolution IR video image rapidly. In some embodiments, a more conservative threshold is chosen for the fast alarm than for the master alarm.

Some embodiments feature a local treatment zone High/Low alarm, where a set of treatment zone High/Low alarm thresholds are adjustable thresholds. In one embodiment, for example, the treatment zone High/Low alarm thresholds may be set to 39° C. and 42° C., respectively. In some embodiments, the treatment zone High/Low alarm is accompanied by a soft audible tone. Two ways of selecting data for determination of treatment zone thresholds include: selecting the entire thermal camera field of view and selecting a subset of the field of view, e.g. a 10 cm diameter area proximate to an aim beam, or other indicator indicative of the area targeted for treatment.

In some embodiments, the dynamic range of thermal cameral 105 may be adjusted to correspond to an expected temperature range for a given surgical application. For example, in some embodiments, the display 115 displays a treatment area within the surgical field 101 and the surgical surroundings. In such embodiments, a temperature range between the surgical surroundings and an expected maximum safe tissue temperature in the treatment area may be 10° C.-80° C. As an example, a typical laser lipolysis treatment may require a range of approximately 20° C.-45° C. for some applications. By tailoring the dynamic range of the camera to the expected temperature range, cost and processing time reduction may be gained.

In some embodiments, a software feature set of the thermal camera may be limited. For example, in some embodiments the camera may not provide 'ON/OFF' controls, may default to display a false color image, and may have only one to three easily set temperature ranges.

Figure 4:
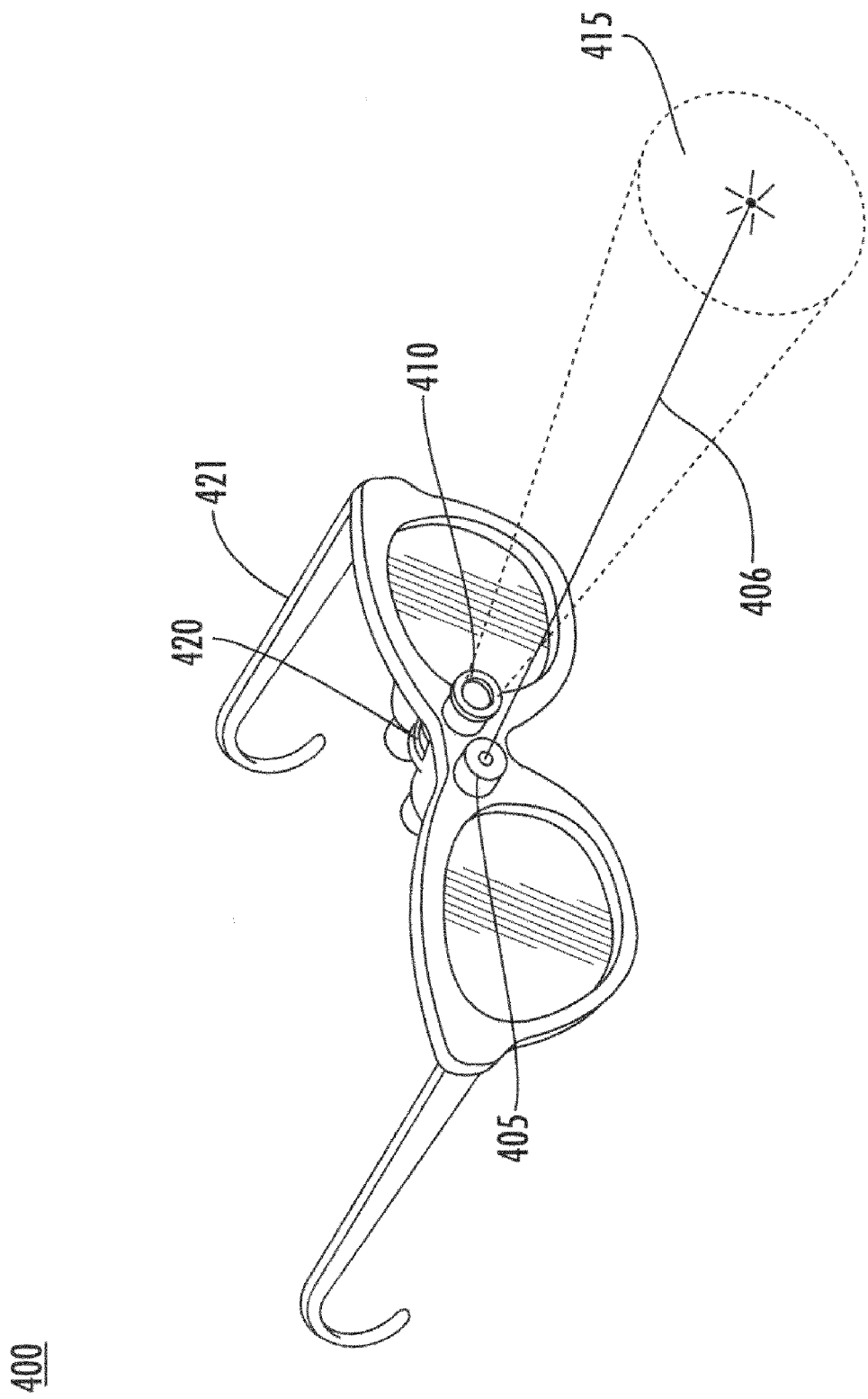
FIG. 4 shows a portable IR sensor for a surgical theatre in accordance with a preferred embodiment of the present invention.

FIG. 4 shows a portable thermal sensor device 400 for a surgical theatre. As shown, device 400 provides for convenient, hands-free temperature monitoring of a surface within a surgical working range. The device incorporates an aim indicator 405, for example, a red, 635 nm laser diode, and an infrared temperature sensor 410, into the frame of a pair of eye glasses 421 or other suitable head set. Aim beam 406 emanating from the aim indicator 405 illuminates a sampling point on a target surface 415 for the IR sensor 410. The IR sensor supplies a temperature corresponding to an approximate area about the aim beam sampling point.

In some embodiments, a threshold adjustment 420 on the pair of eyeglasses 421 or head set allows the user to set a limit where an alarm may sound should the temperature of the indicated area rise above a safe limit. In some embodiments, the aim beam is pulse modulated at a slow, steady blinking rate for a given temperature; for example, a 1 Hz signal at a 50% duty cycle may indicate a temperature of 35° C. As the temperature increases, the frequency may increase; for example, a 5 Hz signal at a 50% duty cycle may indicate a temperature of 40° C. In some embodiments, the pulse modulation rate increases up to a near constant beam at the alarm threshold set point.

Figure 5:
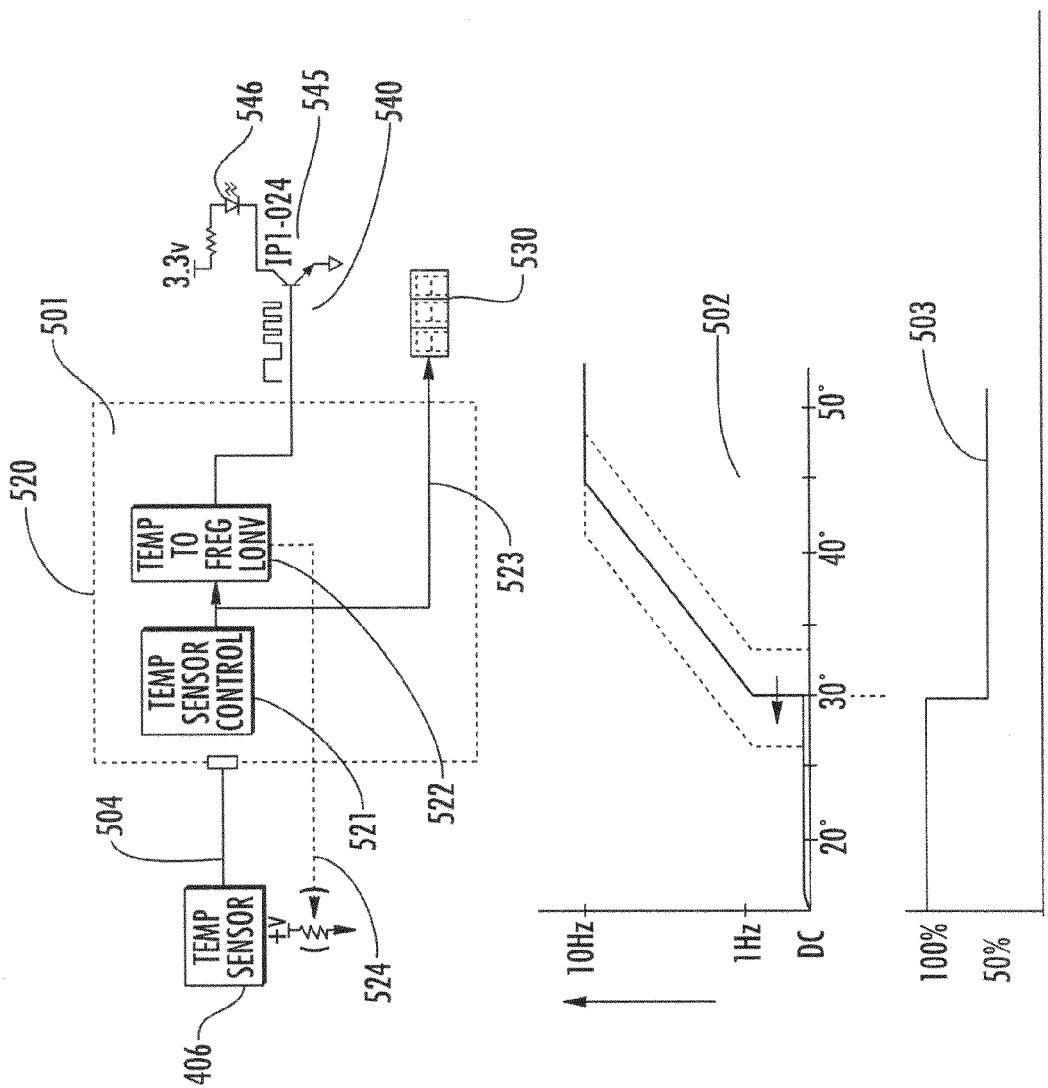
FIG. 5 shows a block diagram for a temperature to frequency converter element of a temperature alarm subsystem in accordance with a preferred embodiment of the present invention, with accompanying performance curves.

FIG. 5 shows a block diagram of a temperature alarm subsystem in accordance with a preferred embodiment of the present invention. The exemplary temperature alarm subsystem circuit 501, shown in FIG. 5, may control aim beam 406 pulse modulation frequency and duty cycle as a function of the temperature of a treatment tissue 309, as described above. Also, presented in FIG. 5: a typical set of plots for pulse modulation frequency 502 and duty cycle 503 vs. a measured temperature 504 of the treatment tissue 309.

A signal from the IR temperature sensor 410 is passed to a microprocessor 520, which includes a temperature sensor control 521 and a temperature to frequency converter 522. In some embodiments, the temperature sensor control 521 converts the measured temperature 504 to a digital numerical data representation 523 of the measured temperature 504. The digital numerical data representation 523 data may be displayed on a temperature display 530, which may be, for example, a three digit digital display.

The digital numerical data representation 523 and a digital offset 524 are input to the temperature to frequency convertor 522, which converts the digital numerical data representation 523 of the measured temperature 504 into a digital pulse signal 540 with a frequency and a duty cycle dependent on the measured temperature 504. The digital pulse signal 540 drives an input transistor 545 to the aim beam 406, thereby turning on and off an aim beam laser diode 546. In various embodiments, some or all of the above described processing may take place in the microprocessor 520.

It is to be understood that, in various embodiments, temperature sensing and display of the type described herein can be incorporated into any number of devices where it is desired, for example, to use an inexpensive, convenient method of scanning an area for hot-spots (or cold spots, or other temperature characteristics, etc.). For example, various embodiments may provide a plastic surgeon with a convenient means to track skin temperature during a laser lipolysis procedure, e.g., of the types described above.

As the treatment beam from a laser lipolysis handpiece gets closer to the surface, the chance of an undesirable outcome (e.g. burning the skin) becomes more probable. If the surgeon has access to a temperature map of the area (e.g., provided by a thermal camera image as described above), hot spots could be identified quickly and the laser stopped or cooling applied. However, for some applications, such cameras may be expensive and integration into the surgeon's set-up may be cumbersome.

For an application of laser lipolysis, the surgeon typically must already wear protective eyewear, therefore adding a sensing and alarm element to the glasses is not only possible, but convenient. Thus for many applications, the portable or hands-free device 400 provides benefits to the surgeon. IR temperature sensor 410 tracks the eyes of the surgeon, sensing temperature in the direct field of view of the surgeon.

In some embodiments, several different preset temperature thresholds may be selected to provide a distinct set of, for example, audible cues at a set of critical measured temperatures. In some embodiments, for example, the target tissue 309 should be maintained within a temperature band. The set of audible cues for the given example may be a pulse modulate tone, where the frequency and duty cycle of the tone can be varied from the low end to the high end of the temperature band. In some embodiments, the frequency of the tone may be a constant and the duty cycle of the tone varied for a measured temperature below the temperature band. In some embodiments, the frequency of the tone may be a constant and the duty cycle of the tone set to 100% for a measured temperature above the temperature band. Of course, any other suitable configurations are possible including cues based on frequency, volume, etc. of the tone. As noted above, in some embodiments cues may be similarly provided by modulating properties of the aim beam (intensity, wavelength, etc.).

Figure 6:
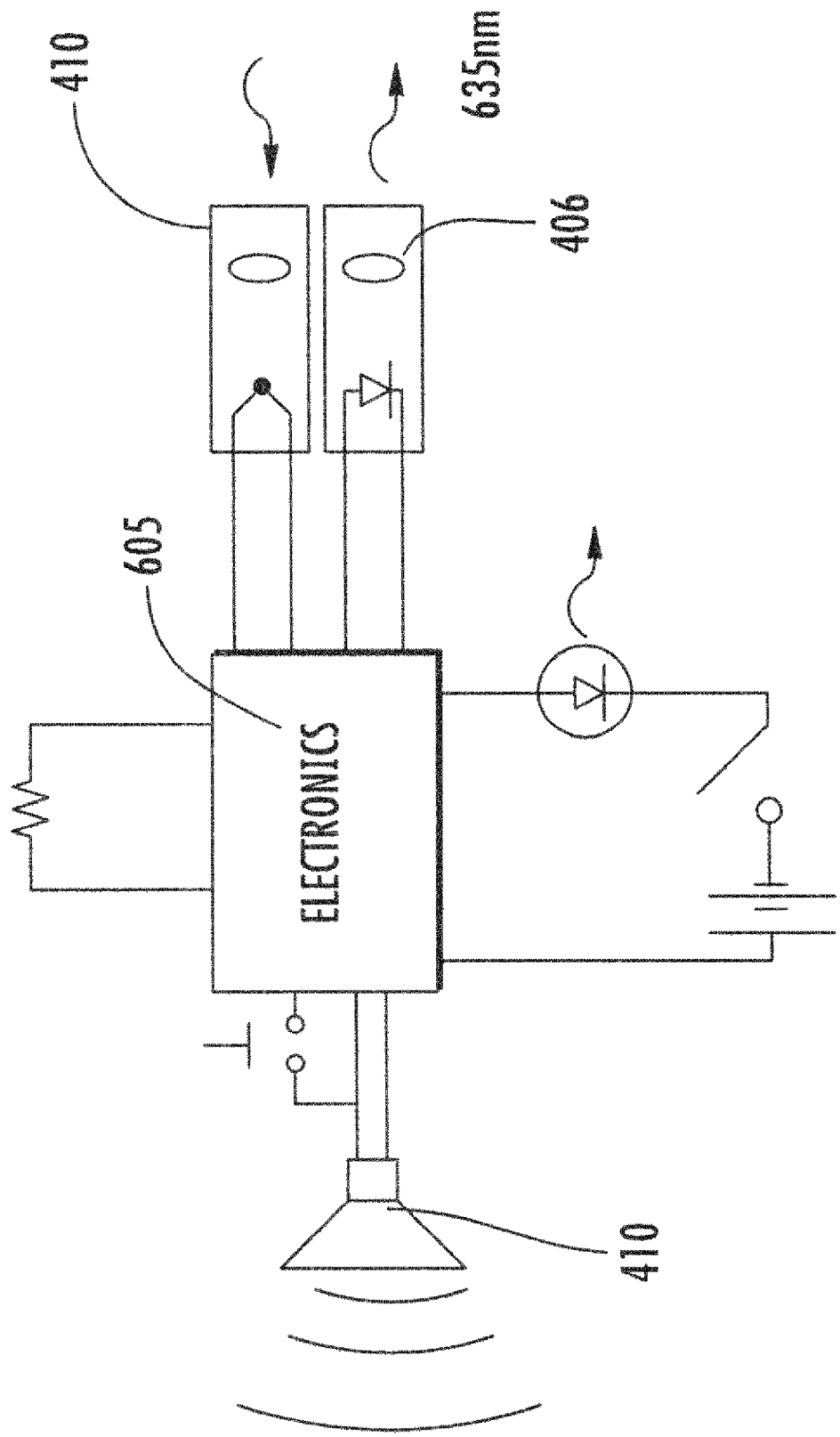
FIG. 6 shows a modulator/alarm test circuit used to confirm that the temperature alarm subsystem is functional and properly calibrated in accordance with a preferred embodiment of the present invention.

FIG. 6 shows a modulator/alarm test circuit used to confirm that the temperature alarm subsystem is functional and properly calibrated. The circuit also includes electronics 605 for processing signals received from the IR sensor 410 and for controlling the output of the aim beam 406 and a tone generating speaker 610. In some embodiments, the modulator/alarm test circuit and the temperature alarm subsystem the system can be battery powered, with the battery resident on the eyeglasses frame 421 or head set.

In some embodiments, a an accelerometer and/or a gyroscope (not shown) may be mounted to the eyeglasses frame 421 or head set to provide position and motion information. In some embodiments, the accelerometer and/or the gyroscope may be a MEMS fabricated device.

For example, in some embodiments, the position and motion information can direct the electronics 605 to turn off power to the laser 125 if the head of the surgeon is not tilted down. In doing so, the possibility of directing the laser 125 into the eyes of a colleague is reduced.

In some situations, a surgeons head must be upright during a surgical procedure. Accordingly, in some embodiments, there is communication between the treatment laser and the eyewear such that aim beam 406 only emits when the treatment is being applied (e.g. when a laser footswitch is pressed). In some embodiments, a treatment laser (e.g. an IR treatment laser) communicates with IR temperature sensor 410 through a signal modulated on to the treatment laser beam, a portion of which is scattered or otherwise directed to the IR sensor (e.g. a remitted, room scattered 5-40 Hz, 1064 nm signal).

In some embodiments, the mechanical layout of the system 400 will involve a design which accounts for parallax errors of the aim beam 406 and the temperature sensor 410. In typical embodiments, there is a preferred working distance where the parallax errors will be reduced or minimized.

Figure 7:
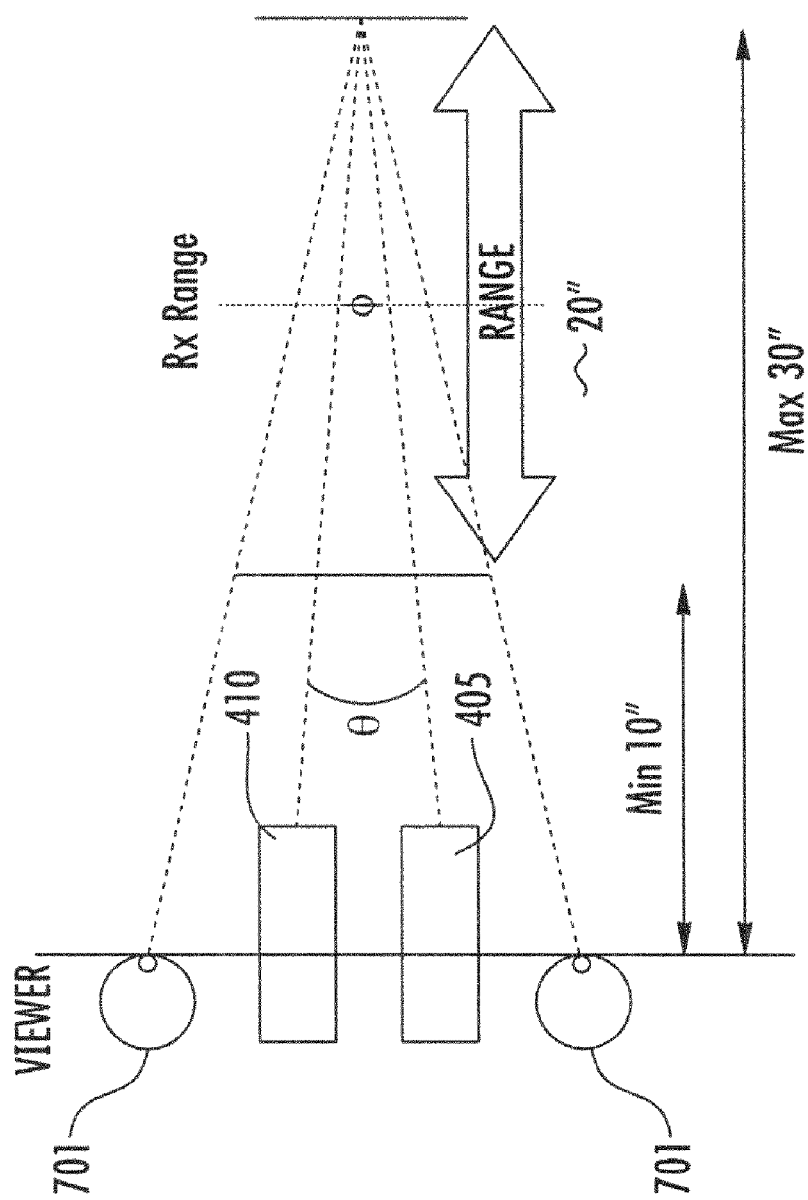
FIG. 7 shows the arrangement of a temperature sensor and aim indicator mounted on eyewear.

For example, FIG. 7 shows the proximity of the aim beam 406 and the sampling point on a target surface 415 for the IR temperature sensor 410 for an exemplary embodiment. Sensor 410 and the source of aim beam 406 are positioned between the eyes 710 of the user to reduce parallax error. The aim beam 406 produces a spot 1-2 mm in diameter at the target surface 415. The viewing area of the IR sensor 410 is about 10 times the spot size at a working distance of 10-30". In some embodiments the viewing area of the sensor may be even smaller to provide improved resolution. In typical applications, good resolution (e.g., <2 cm diameter) at the full working distance is important in allowing the user to trust the modulation frequency and/or alarm.

In one embodiment, the digital numerical data representation 523 of the measured temperature 504 is displayed in an outer visual field of the eyeglasses frame 421 or head set. Such a display may remove any guesswork or interpretation in determining a true temperature for the target surface 415.

One or more or any part thereof of the temperature measurement, feedback, and/or display techniques described above can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis method can also be implemented as a computer-readable storage medium, configured with a computer program, where the storage medium so configured causes a computer to operate in a specific and predefined manner to perform the functions described herein.

A number of embodiments of the invention have been described. Nevertheless, it will be understood that various modifications may be made without departing from the spirit and scope of the invention.

For example, it is to be understood that although in the examples provided above laser light is used for treatment, other sources of treatment light (e.g. flash lamps, light emitting diodes) may be used.

As used herein the term 'light' is to be understood to include electromagnetic radiation both within and outside of the visible spectrum, including, for example, ultraviolet and infrared radiation.

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

All publications, patents, and patent applications mentioned in this specification are herein incorporated by reference to the same extent as if each individual publication, patent, or patent application was specifically and individually indicated to be incorporated by reference.

As noted above, light-based technology is used for cutaneous treatments including the elimination of vascular lesions, hair and wrinkles. Several means are currently available to apply cooling to the skin surface at or around the precise timing of the laser or light source pulse. This cooling spares the epidermal layer and the adds comfort to the patient. The cooling means that are in practice include forced chilled air, cryogen spray and contact cooling of a thermal mass adjacent to the irradiated spot.

Forced chilled air directed at the laser-tissue interface is common practice, but the state of the art involves a large chiller separate from the laser whose dedicated purpose is to generate cold air. The large size of the chiller is required due to the demands on air flow rate (2-10 cfm) and effective temperatures (0-10 F) discharged from the end of a ½" diameter hose that is approximately 2 meters long. In addition, high demand applications such as hair removal may require that the laser (and cooling) be on for 10 hours a day with an 80% duty cycle. The invention described herein represents a unique means for providing skin cooling that advantageously meets the specific needs of laser-tissue interaction.

Figure 8:
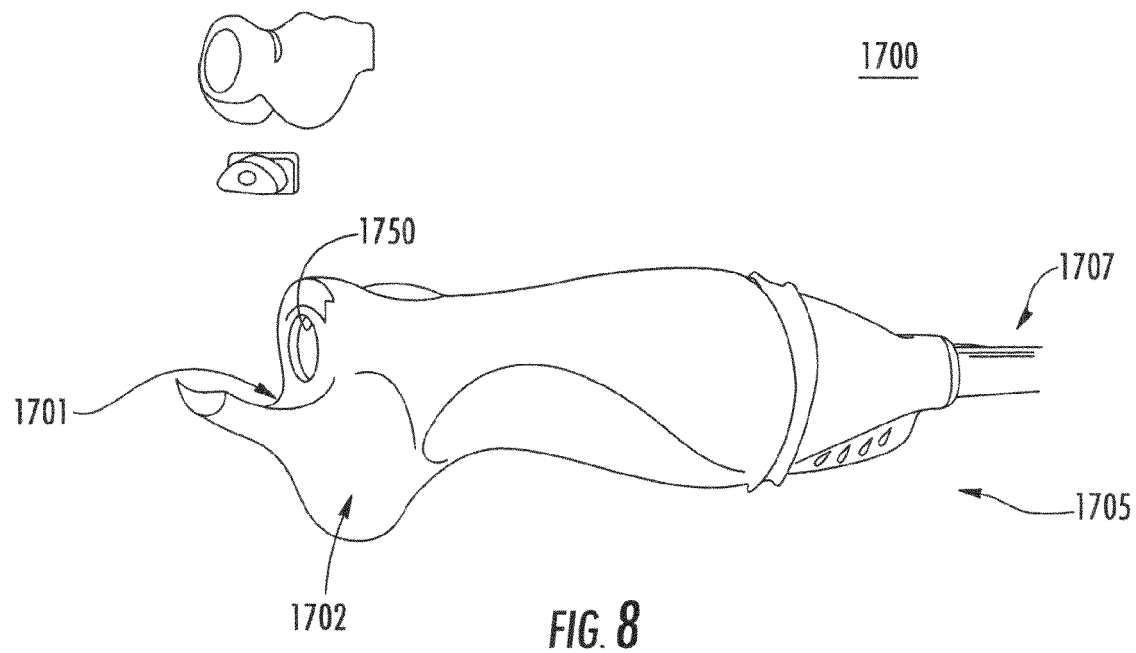
FIG. 8 is an external view of a laser handpiece with an optical delivery assembly using vortex cooler and optional nebulizer.
Figure 9:
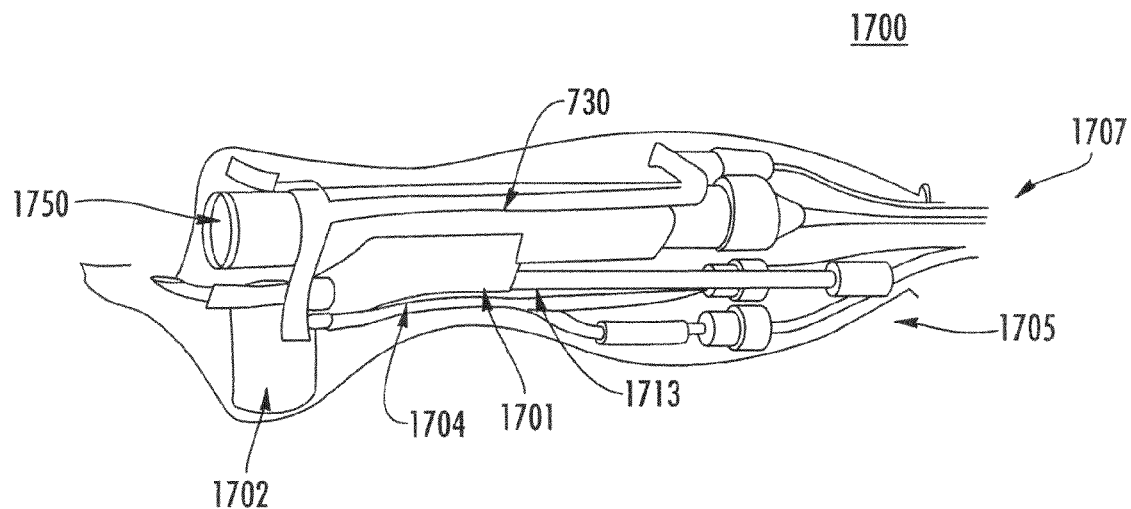
FIG. 9 is an internal view of the laser handpiece.

FIG. 8 is an external view of laser handpiece 1700 with an optical delivery assembly 1750 using vortex cooler 1701 and optional nebulizer 1702. FIG. 9 is an internal view of laser handpiece 1700 using vortex cooler 1701 and optional nebulizer 1701. Vortex cooling is used in industry for a wide range of applications including the cooling of machining operations and removing heat from sewing needles. The mechanism is simple; the concept is relatively complex. Air that rotates around an axis (like a tornado) is called a vortex. A vortex tube 1703 creates cold air and hot air by forcing a simple heat exchange. Compressed air enters a chamber in a tube and is forced to spin in a tight, high speed circular path (1,000,000 RPM). A percentage of the high speed air exits as hot air out the hot exhaust of the tube, but the remainder of the (now slower) air stream is forced to counterflow back up through the center of the high speed air stream, thus giving up heat and exiting as cold air. This method of generating cold air is simple—all that is required is an air compressor and a vortex tube which has no moving parts.

For typical applications, the cooling should be integrated into the laser chassis. This is possible with the vortex cooling method. Vortex cooling, though less efficient than standard refrigeration, enables the heat exchange to happen at the handpiece, not remotely and subsequently transferred by hose to the laser site. Rather than have a large bore, low pressure, insulated delivery hose, the work is delivered to the handpiece via a small bore, high pressure hose. This is important because it affects the ergonomics of the laser handpiece—streamlining the design of the utilities (optical, electrical, pneumatic, etc.) supplied to it. The noise of the exiting air can be addressed by the addition of a muffler 1704, which will add some bulk to the handpiece 1700, but should not be a significant obstacle. The hot fraction of the vortex cooler can be exhausted out the rear of the handpiece—potentially traveling back up the umbilical chord attaching the handpiece to the laser.

The cold fraction of the vortex cooler is directed at the laser site in close proximity to where the laser exposure will be made. The ideal nozzle design for the cold fraction optimizes the coupling of the cold air exchange by disrupting any boundary layer on the skin's surface. The nozzle design should also incorporate a distance gage to fix the distance between the handpiece optics and the image plane. This will simultaneously set the nozzle at the optimum distance to extract heat from the target.

Inlet air humidity is a significant variable in vortex tube performance; a drier in the path between the compressor and the vortex tube can be important. A drier air adds cooling capacity (and hotter exhaust) and in addition, to the surprise of the investigations, increases the flow rate. The drier air also serves to stabilize the output of the chiller under different ambient conditions.

A heat exchanger is required after the compressor to lower the temperature of the post-compressor air as it feeds into the vortex tube. This can be a simple copper coil. Further cooling will occur as the compressed air is shuttled to the handpiece via a 2-3 meter hose 1707 connected to the laser handpiece integrated with a vortex cooler.

Characterization of the present refrigeration-based system has lead to a baseline performance goal. This was done by using a heated block with a known input and characterizing its response to chilled air cooling by means of a thermal camera and thermocouples. Based on this, the vortex discharge air temperature, humidity, and flow rate have been reigned in to be able to compare with the refrigeration-based system. The air temperature on the skin is preferred to be around −10 to 0° C.

A way to augment the cooling effect of the Vortex (or any cooling scheme) is to add an aerosolized source of water vapor to the discharge of the cold air incident on the skin. The latent heat of evaporation of water is −2.2 J/mg—almost 7 times that of melting ice. The application of 50 mg of water in an evaporated mist could counter the effects of a −100 J laser pulse if perfectly coupled to the laser site. The represents a cube of water approximately 4 mm on a side—which may at present be too much to practically aerosolize in one second between pulses, but any fraction of that 50 mg can help For those laser applications which rely on water absorption for the tissue effect, the nebulizer stream can be turned off during the laser pulse and only applied during the off-cycle of the laser. A nebulizer 1702 spraying micron-sized droplets of distilled water in the exit air stream of the handpiece nozzle can significantly add to the effective cooling capacity of the chiller without presenting any water accumulation to the skin's surface since evaporation would have already taken place. The amount of water that can be applied to the air stream to optimize evaporation will be dependent on the air stream properties.

What is claimed is:

1. An apparatus for a thermal surgical procedure comprising: a thermal camera for monitoring temperature at a plurality of patient locations within at least a portion of a surgical field undergoing thermal surgical treatment and generating a series of thermal images based on said thermal monitoring, a video camera for monitoring at least a portion of the surgical field and generating a series of video images in real time based on said video monitoring, a processor for processing the thermal images and video images, wherein the processor:
   i. determines temperature information about the portion of the surgical field based on the thermal images,
   ii. is configured to superimpose the thermal images with the video images to generate a series of display images; and
   iii. is adapted for coupling to a laser surgical device configured to control the operation of the laser surgical device based on said temperature information; and
a display for displaying, in real time, the display images indicative of temperature at the plurality of patient locations.

2. The apparatus of claim 1, wherein the display images indicative of temperature at the plurality of locations comprise false color images.

3. The apparatus of claim 1, wherein the thermal camera is an infrared camera.

4. The apparatus of claim 1, wherein the thermal camera generates the series of thermal images at a rate of greater than about 30 frames per second.

5. The apparatus of claim 1, wherein the display displays the series of display images at a rate of greater than about 30 frames per second.

6. The apparatus of claim 1, wherein the field of view of the thermal camera substantially overlaps the field of view of the video camera.

7. The apparatus of claim 1, further comprising an optical element which selectively directs light from the surgical field in the infrared spectrum to the thermal camera, and selectively directs light from the surgical field in the visible spectrum to the video camera.

8. The apparatus of claim 1, wherein at least one of the thermal camera and the video camera comprise an autofocus.

9. The apparatus of claim 1, further comprising a servo unit for directing the thermal camera to monitor a selected portion of the surgical field.

10. The apparatus of claim 1, wherein the processor is configured to: process the thermal images and determine information indicative of temperature at the plurality of locations; compare the information indicative of temperature at the plurality of locations to a selected master threshold temperature; and produce a master alarm if the temperature at any of the plurality of locations exceeds the selected master threshold temperature.

11. The apparatus of claim 10, wherein the processor is coupled to a laser surgical device and is configured to control the operation of the laser surgical device in response to the master alarm.

12. The apparatus of claim 10, wherein the processor is configured to: process the thermal images and determine information indicative of temperature at a subset of the plurality of locations; compare the information indicative of temperature at the subset of plurality of locations to a selected range of temperature; and produce a range alarm if the temperature at any of the subset of the plurality of locations falls outside the selected range.

13. The apparatus of claim 12, wherein the processor is coupled to a laser surgical device and is configured to control the operation of the laser surgical device in response to the range alarm.

14. The apparatus of claim 10, wherein the processor is configured to: process the thermal images and determine information indicative of a rate of change of temperature at the plurality of locations; compare the information indicative of temperature at the plurality of locations to a selected secondary threshold temperature; compare the information indicative of the rate of change of temperature at the plurality of locations to a selected threshold rate; and produce a rate alarm if, at any one of the plurality of locations, the temperature exceeds the secondary threshold and the rate of change of temperature exceed the rate threshold.

15. The apparatus of claim 14, wherein the processor is coupled to a laser surgical device and is configured to control the operation of the laser surgical device in response to the rate alarm.

16. The apparatus of claim 1, wherein the display comprises at least one chosen from the group consisting of: a video monitor, a flat panel monitor, a heads up display, and a virtual reality display.

17. A method for monitoring a thermal surgical procedure comprising:
   i. using a thermal camera to monitor temperature at a plurality of patient locations within at least a portion of a surgical field undergoing thermal surgical treatment and generating a series of thermal images based on said monitoring;
   ii. using a video camera to monitor at least a portion of the surgical field and displaying in real time video images of said portion of the surgical field, and displaying, in real time, a series of display images comprising a superposition of the video images and the thermal images, where the display images are indicative of temperature at the plurality of patient locations;
   iii. generating feedback information from the display images representative of a temperature characteristic of one or more of the patient locations; and iv. regulating light output from a laser surgical device responsive at least in part to the application of the feedback information.

18. The method of claim 17, wherein the displaying, in real time, a series of display images indicative of temperature at the plurality of positions comprises displaying false color images.

19. The method of claim 17, further comprising: processing the thermal images and determine information indicative of temperature at the plurality of locations; comparing the information indicative of temperature at the plurality of locations to a selected master threshold temperature; and producing a master alarm if the temperature at any of the plurality of locations exceeds the selected master threshold temperature.

20. The method of claim 19, further comprising: processing the thermal images and determining information indicative of temperature at a subset of the plurality of locations; comparing the information indicative of temperature at the subset of plurality of locations to a selected range of temperature; and producing a range alarm if the temperature at any of the subset of the plurality of locations falls outside the selected range.

21. The method of claim 19, further comprising: processing the thermal images and determine information indicative of a rate of change of temperature at the plurality of locations; comparing the information indicative of temperature at the plurality of locations to a selected secondary threshold temperature; comparing the information indicative of the rate of change of temperature at the plurality of locations to a selected rate threshold; and producing a rate alarm if, at any one of the plurality of locations, the temperature exceeds the secondary threshold and the rate of change of temperature exceed the rate threshold.

22. The method of claim 17, further comprising: providing an indicator identifying an area of interest within the surgical field; tracking the position of the indicator; and adjusting the thermal camera to monitor the area of interest.

23. An apparatus for a thermal surgical procedure comprising:
a thermal camera for monitoring temperature at a plurality of patient locations within at least a portion of a surgical field undergoing thermal surgical treatment and generating a series of thermal images based on said thermal monitoring,
a video camera for monitoring at least a portion of the surgical field and generating a series of video images in real time based on said video monitoring,
a processor for processing the thermal images and video images, the processor configured to superimpose the thermal images with the video images to generate a series of display images and generating feedback information from the display images representative of a characteristic of one or more of the patient locations;
a display for displaying, in real time, the display images indicative of temperature at the plurality of patient locations; and
a laser surgical device for generating light for the thermal surgical procedure, wherein the laser surgical device is responsive at least in part to the application of the feedback information to generate the light.

24. The apparatus of claim 23 wherein the feedback information is applied to the surgical device by a user to at least in part control the surgical device.

25. The apparatus of claim 23 wherein the feedback information is applied to the surgical device by the processor to at least in part control the surgical device.

* * * * *